US012601705B2

(12) United States Patent
Karimi et al.

(10) Patent No.: US 12,601,705 B2
(45) Date of Patent: Apr. 14, 2026

(54) SENSOR FOR MEASURING IONIZED MAGNESIUM

(71) Applicant: Instrumentation Laboratory Company, Bedford, MA (US)

(72) Inventors: Anahita Karimi, Westwood, MA (US); Sohrab Mansouri, Sudbury, MA (US)

(73) Assignee: Instrumentation Laboratory Company, Bedford, MA (US)

(*) Notice: Subject to any disclaimer, the term of this patent is extended or adjusted under 35 U.S.C. 154(b) by 369 days.

(21) Appl. No.: 18/107,188

(22) Filed: Feb. 8, 2023

(65) Prior Publication Data

US 2023/0304960 A1 Sep. 28, 2023

Related U.S. Application Data

(60) Provisional application No. 63/308,353, filed on Feb. 9, 2022.

(51) Int. Cl.
*G01N 27/333* (2006.01)
*G01N 33/84* (2006.01)

(52) U.S. Cl.
CPC ....... *G01N 27/3335* (2013.01); *G01N 27/333* (2013.01); *G01N 33/84* (2013.01)

(58) Field of Classification Search
None
See application file for complete search history.

(56) References Cited

U.S. PATENT DOCUMENTS

| | | | |
|---|---|---|---|
| 5,350,518 A | 9/1994 | Hiti et al. | |
| 6,872,297 B2 | 3/2005 | Xu et al. | |
| 10,241,071 B2 | 3/2019 | Zhang et al. | |
| 12,228,565 B2 | 2/2025 | Erdosy et al. | |
| 2004/0211666 A1 | 10/2004 | Pamidi et al. | |
| 2004/0256227 A1 | 12/2004 | Shin et al. | |
| 2010/0012493 A1 | 1/2010 | Murphy et al. | |
| 2018/0024088 A1 | 1/2018 | Benco et al. | |
| 2020/0173955 A1 | 6/2020 | Zhang et al. | |
| 2020/0319134 A1 | 10/2020 | Xu et al. | |
| 2021/0164931 A1* | 6/2021 | Benco | G01N 27/3335 |

FOREIGN PATENT DOCUMENTS

| | | |
|---|---|---|
| WO | 2009157755 A2 | 12/2009 |
| WO | 2020007625 A1 | 1/2020 |

OTHER PUBLICATIONS

International Preliminary Report on Patentability received for PCT Patent Application No. PCT/US2023/012598, mailed on Aug. 22, 2024, 8 pages.

(Continued)

*Primary Examiner* — J. Christopher Ball
(74) *Attorney, Agent, or Firm* — ARENTFOX SCHIFF LLP

(57) ABSTRACT

An example sensor includes a conductive electrode and an ion-selective membrane over the conductive electrode. The ion-selective membrane includes an ionophore that is selective for ionized magnesium (iMg) and at least two types of anionic lipophilic salts. The at least two types of anionic lipophilic salts may include one or more fluorinated borate salts and one or more chlorinated borate salts.

20 Claims, 5 Drawing Sheets

(56) References Cited

OTHER PUBLICATIONS

Buhlmann et al., Influence of natural, electrically neutral lipids on the potentiometric responses of cation-selective polymeric membrane electrodes. Anal Chem. Jul. 15, 2001;73(14):3199-205.
Kappeli et al., Partition of alkane by an extracellular vesicle derived from hexadecane-grown Acinetobacter. J Bacteriol. Nov. 1979;140(2):707-12.
Zhao et al., Effect of surface compositional heterogeneities and microphase segregation of fluorinated amphiphilic copolymers on antifouling performance. ACS Appl Mater Interfaces. Aug. 28, 2013;5(16):7808-18. doi: 10.1021/am401568b. Epub Aug. 6, 2013.
GEM 5000 Blood Gas Analyser. Royal Devon and Exeter Healthcare NHS Trust. SOP. Blood Sciences Laboratory. May 4, 2019. 35 pages.
GEM PremierTM 3500 with iQM. 2023. 13 pages.
GEM Premier ChemSTAT iQM. 2023. 12 pages.
GEM PremierTM 5000. Operator's Manual. P/N 00024029449. Rev. 02. Feb. 2020. 246 pages.
International Search Report and Written Opinion in Application No. PCT/US2023/012598 dated Jun. 1, 2023 (14 pages).
De Almeida et al., "Biosurfactants: Promising Molecules for Petroleum Biotechnology Advances," Frontiers in Microbiology, vol. 7, art. 1718, (2016), 14 pages.
Giannetto et al., "Potentiometric Determination of Non-Ionic Surfactants by Liquid Membrane Electrodes," Electroanalysis, vol. 15, No. 20, pp. 1598-1605 (2003), 8 pages.
Malinowska et al., "Potentiometric response of magnesium-selective membrane electrode in the presence of nonionic surfactants," Analytica Chimica Acta, vol. 382, iss. 3, pp. 265-275 (1999).
Pal et al., "Scientific information about sugar-based emulsifiers: a comprehensive review," RSC Advances, vol. 11, pp. 33004-33016, (2021), 13 pages.
Puelles, J. G. S., "Hematite Flotation using a crude biosurfactant extracted from Rhodococcus opacus," Maxwell System, Pontifical Catholic University of Rio de Janeiro, URL: https://www.maxwell.vrac.puc-rio.br/colecao.php?strSecao=resultado&nrSeq=29688@2, (2017), 25 pages.
Ron et al., "Biosurfactants and oil bioremediation," Current Opinion in Biotechnology, vol. 13, pp. 249-252, DOI:10.1016/S0958-1669(02)00316-6, (2002), 4 pages.
Singh et al., "Biosurfactant production: Emerging trends and promising strategies," Journal of Applied Microbiology, vol. 126, pp. 2-13, (2018), 12 pages.
Zhang et al., "A comparison of neutral Mg2+-selective ionophores in solvent polymeric membranes: complex stoichiometry and lipophilicity," Analytical Sciences, vol. 16, iss. 1, pp. 11-18 (2000), 8 pages.

* cited by examiner

SENSOR FOR MEASURING IONIZED MAGNESIUM

CROSS-REFERENCE TO RELATED APPLICATION

This application claims the benefit of, and priority to, U.S. Provisional Application No. 63/308,353, which was filed on Feb. 9, 2022. The contents of U.S. Provisional Application No. 63/308,353 are incorporated herein by reference.

TECHNICAL FIELD

This specification relates generally to example electrochemical sensors, which may include ion-selective electrodes (ISE) for measuring an amount of ionized magnesium (iMg) in a biological fluid.

BACKGROUND

A biological fluid such as blood, or a component or derivative thereof, contains magnesium (Mg). Ionized magnesium (iMg) constitutes about 59% to 72% of the total Mg in such a fluid and represents the physiologically active portion of the total Mg. About 5% to 11% of the magnesium in the fluid is complexed with anions. The remaining 23% to 31% of the magnesium in the fluid is bound to protein.

The amount of iMg in a biological fluid such as blood may be a marker for a medical condition such as dysmagnesemia or an electrolyte deficiency, for example. Tests have therefore been developed to estimate the amount of iMg in a biological fluid.

For a healthy patient that is not under stress, there is a standard correlation between iMg and total Mg in the patient 's blood. Heretofore, the total amount of Mg in a patient's blood was measured and the iMg portion thereof was estimated based on this correlation. However, when a patient is under stress, such as in a point-of-care (POC) setting like an emergency room, the composition of biological fluids such as blood may vary. For example, stress may cause changes in blood pH, blood serum protein levels, or anions in the blood, which may cause iMg levels to fluctuate. Changes such as these may alter the ratio of iMg to total Mg in a patient's blood. As a result, measurements of the total amount of Mg in a patient's blood may not be an accurate reflection of the amount of iMg in the patient's blood in POC (or other) settings.

SUMMARY

An example sensor includes a conductive electrode and an ion-selective membrane over the conductive electrode. The ion-selective membrane includes (i) an ionophore that is selective for ionized magnesium (iMg) and (ii) at least two types of anionic lipophilic salts. The sensor may include one or more of the following features, either alone or in combination.

The at least two types of anionic lipophilic salts may include one or more fluorinated borate salts. The at least two types of anionic lipophilic salts may include one or more chlorinated borate salts. The at least two types of anionic lipophilic salts may include a mixture of one or more chlorinated borate salts and one or more fluorinated borate salts. The ion-selective membrane may include 1% to 3% weight-by-weight (w/w) of the mixture of one or more chlorinated borate salts and one or more fluorinated borate salts. The one or more chlorinated borate salts may include at least one of: potassium tetrakis(4-chlorophenyl)borate (KTpClPB) or sodium tetrakis(4-chlorophenyl)borate). The one or more fluorinated borate salts may include at least one of: tetrakis(4-fluorophenyl)boron sodium (Cesibor), sodium or potassium tetrakis[3,5-bis(trifluoromethyl)phenyl]borate (NaTPB or KTFPB), or sodium or potassium tetrakis[3,5-bis(1,1,1,3,3,3-hexafluoro-2-methoxy-2-propyl)phenyl]borate trihydrate (HFPB).

The ion-selective membrane may include a plasticizer. The plasticizer may have a log P (partition coefficient) value of between 6.7 and 8.9. The ion-selective membrane may include 60% to 66% weight-by-weight (w/w) of the plasticizer. The plasticizer may include ETH 8045 where ETH 8045 is $C_{26}H_{37}NO_3$ ([12-(4-Ethylphenyl)dodecyl]2-nitrophenyl ether); or a mixture containing ETH 8045 and NPOE, where NPOE is $C_{14}H_{21}NO_3$ (1-(2-Nitrophenoxy)octane); or a mixture com containing ETH 8045 and ETH 217, where ETH 217 is $C_{18}H_{29}NO_3$ (1-Dodecyloxy-2-nitrobenzene, 2-Nitrophenyl dodecyl ether); or a mixture containing ETH 8045, ETH 217, and NPOE.

The ion-selective membrane may include one or more ionophores. The ion-selective membrane may include 1% to 4% weight-by-weight (w/w) of the one or more ionophores. The one or more ionophores may include ETH 5506 where ETH 5506 is $C_{63}H_{96}N_6O_6$ (1,3,5-Tris[10-(1-adamantyl)-7,9-dioxo-6,10-diazaundecyl]benzene); or ETH 7025, where ETH 7025 is $C_{49}H_{94}N_6O_6$ (N,N',N"-Tris[3-(heptylmethylamino)-3-oxopropionyl]-8,8'-iminodioctylamine); or K22B5, where K22B5 is $C_{38}H_{60}N_4O_8$ (4,13-[Bis(N-adamantylcarbamoyl)acetyl]-1,7,10,16,tetraoxa-4,13-diazacyclooctadecane);

The ion selective membrane may include an inner membrane that includes a hydrogel, and an outer membrane that includes the ionophore that is selective for Mg, the least two types of anionic lipophilic salts, a plasticizer, and a polymeric matrix.

An example cartridge may include a sensor that includes a conductive electrode and an ion-selective membrane over the conductive electrode. The ion-selective membrane includes (i) an ionophore that is selective for iMg and (ii) at least two types of anionic lipophilic salts. The cartridge may include a reagent that includes a biosurfactant.

The biosurfactant may include at least one of a high molecular weight biosurfactant or a low molecular weight biosurfactant. The low molecular weight biosurfactant may include at least one of a rhamnolipid, a sophorolipid, or a lipopeptide. The high molecular weight biosurfactant may include at least one of a polysaccharide, a lipopolysaccharide, a protein, or a lipoprotein.

The sensor may include a sample path adjacent to the ion-selective membrane. The cartridge may include a fluid path that runs from at least one or a location at which a test sample is introduced into the cartridge or a location of the regent to the sample path.

An example test system may include a test instrument to receive the cartridge. The sensor may include a conductive electrode having an electrical potential that is based on an activity of the iMg in the test sample. The test system may include an electrical contact to measure the electrical potential. One or more processing devices may be configured to determine the amount of Mg in the test sample based on the electrical potential. The system may be part of, may be, or may include a point-of-care clinical analyzer system.

Any two or more of the features described in this specification, including in this summary section, can be combined to form implementations not specifically described herein.

The details of one or more implementations are set forth in the accompanying drawings and the description below. Other features, objects, and advantages will be apparent from the description and drawings, and from the claims.

DESCRIPTION OF THE DRAWINGS

Like reference numerals in different figures indicate like elements.

DETAILED DESCRIPTION

Described herein are example implementations of ionized magnesium (iMg) sensors that are configured to directly measure the activity of iMg in a sample of biological fluid such as whole blood, which corresponds to the amount of Mg in the fluid. Biofouling has been an issue in implementing iMg sensors of this type. Biofouling includes adsorption of lipids and proteins onto a sensing membrane of an iMg sensor, which can adversely affect sensor performance. In addition, membrane instability has been an issue in implementing iMg sensors of this type. This instability results from loss of membrane components over time. The instability of the membrane may affect both the performance of an iMg sensor and its use-life.

The iMg sensors described herein include an ion-selective (ISE) membrane containing at least two types anionic lipophilic salts. Examples of the two types anionic lipophilic salts include fluorinated anionic lipophilic salts and chlorinated anionic lipophilic salts. The fluorinated anionic lipophilic salts have low surface energy that may hinder or prevent non-specific binding in a biological fluid, which can reduce interaction of the membrane with biofouling compounds and proteins. By reducing or eliminating such interactions, the accuracy and precision of iMg measurements made using the iMg sensor may be increased relative to sensors that do not include fluorinated anionic lipophilic salts. The chlorinated anionic lipophilic salts may contribute to stable ion selectivity and Nernstian response of the iMg sensor over a use-life of the iMg sensor.

iMg includes magnesium (Mg) that has any net electric charge. Mg is found in group two of the periodic table, so an Mg ion is likely to have a two plus (2+) charge. For example $Mg^{2+}$ is a type of iMg that is the second most abundant divalent metal ion within bodily cells, including bodily fluids.

The biological fluid in which iMg may be measured by the iMg sensor may be, or include, any bodily fluid, such as whole blood ("blood") or a component or derivative thereof. Examples of such components or derivatives include, but are not limited to, blood plasma and fluids containing red blood cells extracted from blood. The examples presented below use the word "test sample" to refer to any biological fluids such as these blood-based fluids or other non-blood-based fluids.

Figure 1:
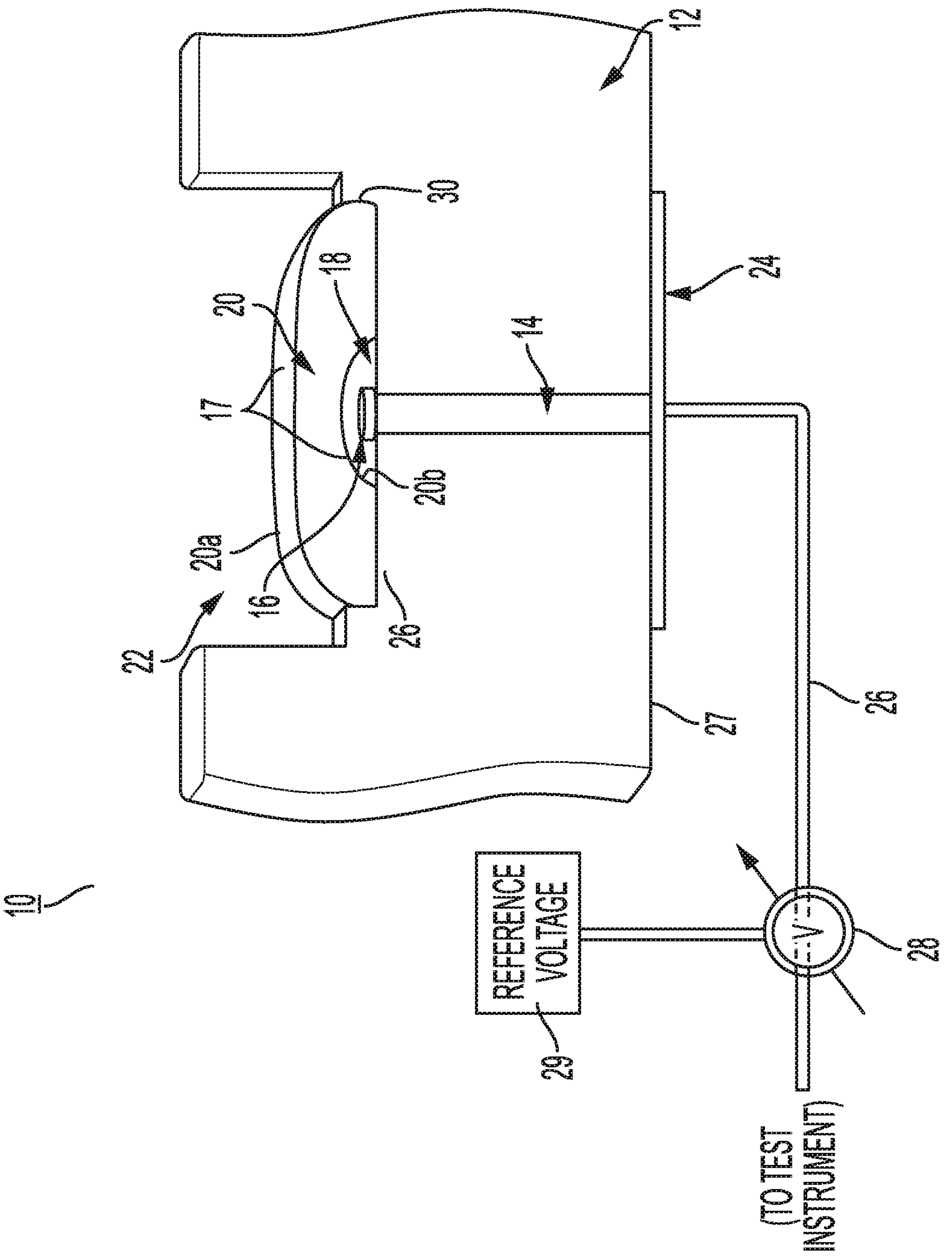
FIG. 1 is block diagram showing an example implementation of an iMg sensor.

FIG. 1 shows an example of an iMg sensor 10. iMg sensor 10 includes a composite membrane 17, an internal electrode 16, a pin 14, and a structure 24, all of which reside on a sensor card 12. In operation, a test sample passes through a channel defining a sample path 22 of iMg sensor 10. Mg ions in the test sample bind with the composite membrane 17 and develop electrical potential. Internal electrode 16, pin 14, and structure 24 are electrically connected and a volt meter 28 is connected to structure 24 to measure this electrical potential.

iMg sensor 10 therefore is a transducer that converts activity of Mg ions in the test sample into a measurable electrical potential. The electrical potential is proportional to the logarithm of the activity of the Mg ions in the test sample according to the Nernst equation. The Nernst equation relates measured electrical potential, known temperature and pressure, and iMg activity or amount. Therefore, the activity or amount of iMg in the test sample can be determined based on a measurement of the electrical potential obtained from iMg sensor 10 by volt meter 28.

Sensor card 12 holds the components of iMg sensor 10. Sensor card 12 may be a non-electrically-conductive substrate. For example, sensor card 12 may be or include a polymeric material such as polyvinyl chloride. However, other non-electrically-conductive materials may be used, such as ceramic or silicon.

Internal electrode 16, pin 14, and structure 24 are all electrically conductive and enable an electrical connection between composite membrane 17 and volt meter 28.

In this example, pin 14 resides within a hole through sensor card 12 and extends from surface 26 to surface 27 of sensor card 12. In some implementations, pin 14 may be made of, or include, silver (Ag) coated with silver chloride (AgCl). In some implementations pin 14 may be made of, or include, other or additional electrically-conductive materials such as gold (Au) or platinum (Pt).

In this example, internal electrode 16 may be located at surface 26 of sensor card 12. Internal electrode 16 may be part of pin 14 or a different component than pin 14. Internal electrode 16 may be made of the same, or different electrically-conductive material as pin 14 such as silver, silver chloride, gold, and/or platinum. In any case, internal electrode 16 and pin 14 may be physically connected to create an electrical connection between the two of them.

In this example, structure 24 is located at a surface 27 of sensor card. Structure 24 may be an electrode that is flat (e.g., a plate) and may cover part of surface 27. In some implementations, structure 24 may have a different shape than flat. For example, the structure may have ridges, peaks, valleys, or other structural features and/or may cover an entirety of surface 27. Structure 24 may be made of any electrically-conductive material. In example Mg sensor 10, structure 24 is printed silver; however, other conductive materials such as gold or platinum may be used.

Structure 24 is physically connected to pin 14 to create an electrical connection between structure 24 and pin 14, thereby also creating an electrical connection between structure 24 and internal electrode 16. Volt meter 28 is electrically connected to both structure 24 and a reference voltage 29. The reference voltage 29 may be produced by a standard reference electrode (see, e.g., FIG. 2) that generates the reference voltage for sensor measurement. The iMg sensor electrode potential then can be measured versus the reference electrode voltage 25. The voltage source that produces the reference voltage may be part of iMg sensor 10.

Mg sensor 10 includes a composite membrane 17 that is on the surface of internal electrode 16. In some implementations, composite membrane 17 includes an inner membrane 18 and an outer membrane 20.

Inner membrane 18 covers, and contacts, internal electrode 16, thereby creating an interface and an electrical connection between outer membrane 20 and internal electrode 16. Inner membrane 18 may be an ionic conductive hydrogel. In a non-limiting example, a composition of this hydrogel includes 2 mM (millimolar) sodium (Na), 5 mM potassium (K), 0.75 mM calcium (Ca), 0.55 mM Mg, and 4.6 mM chloride in a hydroxyethylcellulose solution at 1.1 wt % (percent by weight). Polymer-based hydrogels may also be used to provide a highly permeable conductive matrix between outer membrane 20 and internal electrode 16. Examples of such hydrogels that may be used include, but are not limited, polypyrrole, polyaniline, and poly(ethylenedioxy thiophene) based hydrogels.

Outer membrane 20 covers, and contacts, inner membrane 18 and provides an electrical connection to inner membrane 18. In this example, outer membrane 20 also contacts parts 30 of sensor card 12, for example to ensure that the entirety of inner membrane 18 is covered by outer membrane 20. In some implementations, outer membrane 20 includes a polymeric matrix, an ion-exchanger (ionophore) that is selective for Mg, a plasticizer, and one or more anionic lipophilic salt components. In this regard, lipophilicity refers to the ability of the salt to dissolve in fats, oils, lipids, or non-polar solvents.

In some implementations, the polymeric matrix may include a polymer such as, but not limited to, high molecular weight poly(vinylchloride) (PVC—$(CH_2CHCl)_n$) or carboxylated PVC ($C_5H_7ClO_2$) and a solvent such as, but not limited to, tetrahydrofuran (THF—$C_4H_8O$ or $(CH_2)_3CH_2O$) or cyclohexanone ($C_6H1_0O$). In some implementations, the polymers may be 30%-33% (w/w—weight-by-weight) of the polymeric matrix, however, sensor 10 is not limited to a polymeric matrix having this composition.

Outer membrane 20 also includes one or more ionophore(s) that are selective for iMg. Ionophores are lipophilic complexing agents capable of reversibly binding ions. Ionophore selectivity is based on selective interaction with ions having a certain ionic radius, charge, polarity, and polarizability. In outer membrane 20, the ionophore(s) are selective for Mg, and form(s) complexes with Mg which create a potential difference (a voltage) across two sides 20*a*, 20*b* of outer membrane 20. The potential difference that is created across outer membrane 20 is based on the level of activity of Mg ions in the test sample. In some implementations, the ionophore(s) may be within a range of 1% to 4% w/w of outer membrane 20; however, sensor 10 is not limited to an outer membrane 20 having 1% to 4% w/w ionophore(s).

Examples of ionophores that may be included in outer membrane 20 include, but are not limited to, one or more of the following.

ETH 5506, where ETH 5506 is $C_{63}H_{96}N_6O_6$ (1,3,5-Tris[10-(1-adamantyl)-7,9-dioxo-6,10-diazaundecyl]benzene) and has the following structural formula:

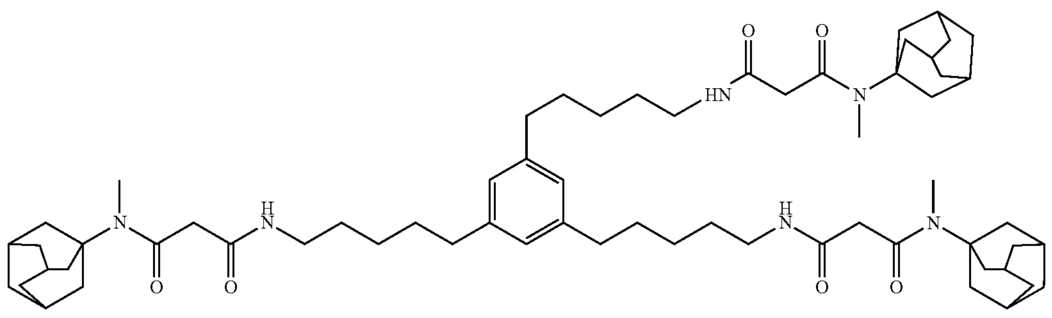 [SMILES: CN(C(=O)CC(=O)NCCCCCc1cc(CCCCCNC(=O)CC(=O)N(C)C23CC4CC(CC(C4)C2)C3)cc(CCCCCNC(=O)CC(=O)N(C)C23CC4CC(CC(C4)C2)C3)c1)C12CC3CC(CC(C3)C1)C2]

ETH 7025, where ETH 7025 is $C_{49}H_{94}N_6O$, (N,N',N"-Tris[3-(heptylmethylamino)-3-oxopropionyl]-8,8'-iminodioctylamine) and has the following structural formula:

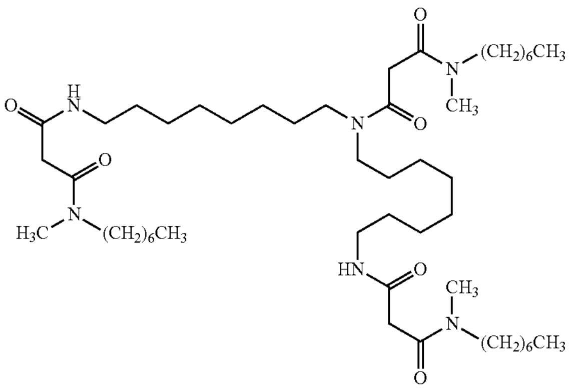

K22B5, where K22B5 is $C_{38}H_{60}N_4O_8$ (4,13-[Bis(N-adamnantylcarbamnoyl)acetyl]-1,7,10,16,tetraoxa-4,13-diazacyclooctadecane) and has the following structural formula:

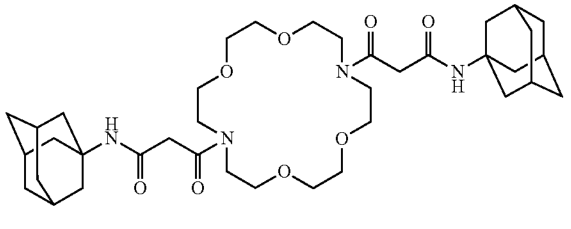 [SMILES: O=C(CC(=O)N1CCOCCOCCN(C(=O)CC(=O)NC23CC4CC(CC(C4)C2)C3)CCOCCOCC1)NC12CC3CC(CC(C3)C1)C2]

Outer membrane 20 can include any one or more of the ionophores listed above either alone or in combination. Outer membrane 20 can also include other ionophores not listed herein, either alone or in combination with those listed.

Outer membrane 20 also includes a plasticizer. A plasticizer is a substance that is added to membrane 20 to make membrane 20 more flexible, e.g., to increase its plasticity and to facilitate ion diffusion. The plasticizer may include a solvent. The type and amount of plasticizer in outer membrane 20 may be selected to support the stability of iMg sensor 10 for a predetermined period of time during use of the iMg sensor. In a non-limiting example, the predetermined period of time may be 30 days, or longer in some examples. The plasticizer may include functional groups that affect the electrical polarity of membrane 20 and the ion selectivity of membrane 20 by facilitating ion dehydration processes. The plasticizer also acts as an organic solvent for membrane 20 and directly affects extraction properties of membrane 20. Plasticizer is the largest portion of the membrane components and its properties including its dielectric constant and lipophilicity can impact ionized magnesium interaction with the membrane.

The usable lifetime of outer membrane 20 is, to a large extent, dictated by the loss of membrane components into the test sample. Membrane lipophilicity may be adjusted to achieve a desired selectivity and stability. The plasticizers that support stability may have a required lipophilicity that, together with anionic lipophilic salt(s), maintain stability and selectivity of outer membrane 20 and extend the use-life of outer membrane 20, e.g., to 30 days or more. In an example, outer membrane 20 may include 60% to 66% w/w plasticizer or plasticizer mixture, each having a log P (partition coefficient) value(s) of between 6.7 and 8.9; however, outer membrane 20 is not limited to these percentages of plasticizer or plasticizer mixture having this range of log P value(s). In this regard, the log P value is a ratio of the compound's organic (oil)-to-aqueous phase concentrations, and is a measure of how hydrophilic or hydrophobic a molecule is.

Examples of plasticizer that may be included in outer membrane 20 include, but are not limited to, one or more of the following:

ETH 8045, where ETH 8045 is $C_{26}H_{37}NO_3$ ([12-(4-Ethylphenyl)dodecyl]2-nitrophenyl ether) and has the following structural formula:

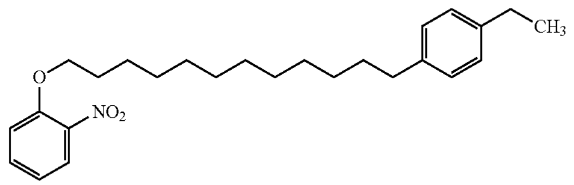 [SMILES: CCc1ccc(CCCCCCCCCCCCOc2ccccc2[N+](=O)[O-])cc1]

a mixture of ETH 8045 and NPOE, where NPOE is $C_{14}H_{21}NO_3$ (1-(2-Nitrophenoxy)octane/nitrophenyl octyl ether) and has the following structural formula:

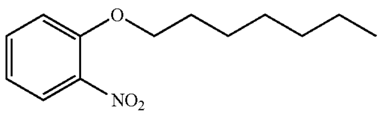 [SMILES: CCCCCCCOc1ccccc1[N+](=O)[O-]]

a mixture of ETH 8045 and ETH 217, where ETH 217 is $C_{18}H_{29}NO_3$ (1-Dodecyloxy-2-nitrobenzene, 2-Nitrophenyl dodecyl ether) and has the following structural formula:

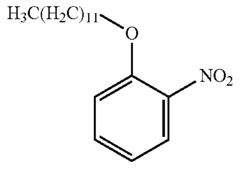

a mixture of ETH 8045, ETH 217, and NPOE

Outer membrane 20 can include any one or more of the plasticizers listed above either alone or in combination. Outer membrane 20 can also include other plasticizers not listed herein, either alone or in combination with those listed.

Outer membrane 20 also includes one or more anionic lipophilic salts. Anionic lipophilic salts may significantly reduce bulk membrane resistance and charge transfer resistance at the interface between membrane 20 and the test sample, e.g., at side 20*a* of membrane 20. The anionic lipophilic salts may ensure electroneutrality of membrane 20 and avoid co-ion extraction, e.g., extraction of more than one type of ion.

An example anionic lipophilic salt includes an ionized salt having increased solubility in lipidic vehicles relative to their free base or acid forms. In some implementations, the anionic lipophilic salts may include a fluorinated anionic lipophilic salt such as fluorinated borate salt, a chlorinated anionic lipophilic salt such as a chlorinated borate salt, a mixture of two or more fluorinated anionic lipophilic salts such as two or more fluorinated borate salts, a mixture of two or more chlorinated anionic lipophilic salts such as two or more chlorinated borate salts, or a mixture of two or more types of anionic lipophilic salts, such as a mixture of one or more fluorinated borate salts and one or more chlorinated borate salts. A fluorinated borate salt includes compounds containing borate or complex borate ions along with fluoride that form salts with cations such as metals. A chlorinated borate salt includes compounds containing borate or complex borate ions along with chlorine that form salts with cations such as metals.

Examples of fluorinated borate salts that may be included in outer membrane 20 include, but are not limited to one or more of the following: tetrakis(4-fluorophenyl)boron sodium (Cesibor), sodium or potassium tetrakis[3,5-bis(trifluoromethyl)phenyl]borate (NaTPB or KTFPB), and/or sodium or potassium tetrakis[3,5-bis(1,1,1,3,3,3-hexafluoro-2-methoxy-2-propyl)phenyl]borate trihydrate (HFPB).

Sodium tetrakis(4-fluorophenyl)borate dihydrate has the following structural formula:

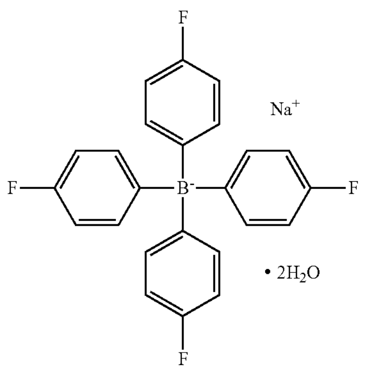 [SMILES: Fc1ccc([B-](c2ccc(F)cc2)(c2ccc(F)cc2)c2ccc(F)cc2)cc1 ; [Na+]]

sodium or potassium tetrakis[3,5-bis(trifluoromethyl)phenyl]borate (NaTPB or KTFPB) has the following structural formula:

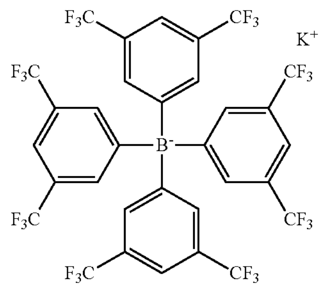 [SMILES: FC(F)(F)c1cc([B-](c2cc(C(F)(F)F)cc(C(F)(F)F)c2)(c2cc(C(F)(F)F)cc(C(F)(F)F)c2)c2cc(C(F)(F)F)cc(C(F)(F)F)c2)cc(C(F)(F)F)c1 ; [K+]]

sodium or potassium tetrakis[3,5-bis(1,1,1,3,3,3-hexafluoro-2-methoxy-2-propyl)phenyl]borate trihydrate (HFPB) has the following structural formula:

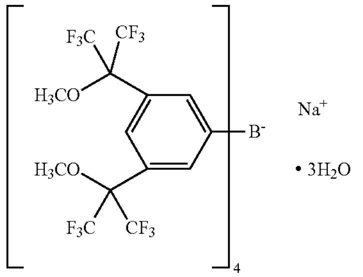

Examples of chlorinated borate salts that may be included in outer membrane 20 include, but are not limited to, potassium tetrakis(4-chlorophenyl)borate (KTpClPB) and/or sodium tetrakis(4-chlorophenyl)borate) KTpClPB has the following structural formula.

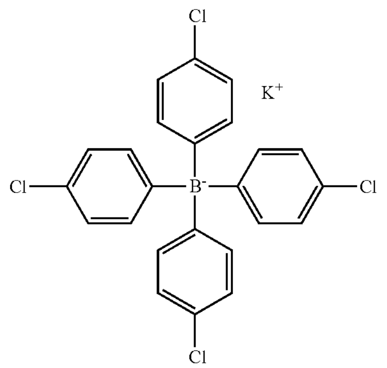 [SMILES: Clc1ccc([B-](c2ccc(Cl)cc2)(c2ccc(Cl)cc2)c2ccc(Cl)cc2)cc1 ; [K+]]

The relative amounts of anionic lipophilic salt and ionophore in outer membrane 20 can affect the ion selectivity of outer membrane 20 for Mg ions. In some examples, outer membrane 20 includes a 1% to 3% (w/w) or, in more particular examples a 1.9% to 2.1% (w/w), mixture containing both fluorinated and chlorinated borate salts. In some implementations, the ratio of fluorinated borate salts to chlorinated borate salts in outer membrane 20 is 1:1. However, outer membrane 20 is not limited to this ratio of fluorinated borate salts to chlorinated borate salts or to the above weight percentages. For example, other ratios may be 1.5:1, 2:1, or more favoring either salt.

Fluorinated anionic lipophilic salts (e.g., potassium tetrakis[3,5-bis(trifluoromethyl)phenyl]borate) in membrane 20 may reduce or eliminate interference in membrane 20's iMg selectivity caused by biofouling relative to membranes that do not include fluorinated anionic lipophilic salts, as described above. One or more fluorinated borate salts in membrane 20 may reduce or eliminate protein or lipid interference in iMg measurements relative to membranes that do not include anionic lipophilic salts. That is, the anti-biofouling property of fluorinated borate salts may hinder or eliminate binding of proteins or lipids to outer membrane 20, which can interfere with iMg measurement. Accordingly, the fluorinated anionic lipophilic salts in outer membrane 20 may improve the precision and accuracy of Mg sensor 10.

Anionic lipophilic salts and other components of example outer membrane 20 may prolong the stability of Mg sensor 10. Stability may be measured by Mg sensor 10 retaining a consistent amount of iMg selectivity and Nernstian response over a period of time. For example, one or more chlorinated borate salts in membrane 20 may contribute to stable iMg selectivity and a stable Nernstian response over a predetermined use life of the iMg sensor, as explained previously.

In some examples, the performance of Mg sensor 10 depends on the type and amount of anionic lipophilic salts (e.g., fluoro- and chloro-anionic lipophilic salts) in membrane 20. The effect of the use of a mixture of fluoro- and chloro-anionic lipophilic salts on the performance accuracy, precision and stability of iMg sensor 10 can be explained with respect to the thermodynamically feasible selection of Mg ions by outer membrane 20, where Mg ion dehydration is catalyzed and biofouling is hindered. Stability of the Nernstian slope of membrane 20 and the ion selectivity of membrane 20 using a mixture of fluoro- and chloro-anionic lipophilic salts may be a result of a decrease in solubility of additives from solvent in outer membrane 20 into the test sample.

Anionic lipophilic salts may also decrease the electrical resistance of outer membrane 20 relative to membranes that do not include anionic lipophilic salts, thereby facilitating transport of the Mg ions to internal electrode 16.

Outer membrane 20 thus may be configured—for example, the composition of outer membrane 20 may be selected and optimized—to facilitate transport of the Mg ions while maintaining sensor stability, sensor accuracy, and sensor precision by selections of the plasticizer and plasticizer proportions, ionophore and ionophore proportions, and borate salts and borate salts proportions. For example, through selection and optimization of the types of anionic lipophilic salts, plasticizers, and concentrations thereof that make up membrane 20, the stability of iMg sensor 20 may be maintained for at least a predefined time, such as 30 days of use or a nine month shelf-life. In some implementations, to improve performance of the iMg sensor during use, the lipophilicity of the plasticizer in the iMg membrane may be adjusted to achieve a desired selectivity and stability, e.g., by using a plasticizer or plasticizer mixture with a log P value of greater than 6.7 and less than 8.9.

In a non-limiting example implementation of iMg sensor 10, outer membrane 20 has the composition shown in Table 1 below. In this example, outer membrane 20 includes PVC as an inert organic polymeric matrix, ETH 5506 as an ionophore, a 1:1 mixture of ETH 8045 and NPOE as plasticizers, and a 1:1 mixture of KTFPB and KTPClPB as anionic lipophilic salts. All of these outer membrane 20 components are dissolved in a THF solvent and have the following weight percentages ("% wt") in membrane 20, excluding the THF solvent. In this example, the lipophilic anionic salts are 150 mol % relative to the ionophore to enable a target iMg selectivity.

TABLE 1

| | IMg MEMBRANE 20 COMPONENTS | % WT |
|---|---|---|
| POLYMERIC MATRIX | PVC | 32 |
| PLASTICIZER | ETH 8045 and NPOE | 64 |
| SALTS | KTFPB and KTpCIPB | 2 |
| IONOPHORE | ETH 5506 | 2 |

Referring back to FIG. 1, outer membrane 20 and sensor card 24 define a sample path 22 of Mg sensor 10. That is, a liquid test sample, such as those described herein, is applied through sample path 22 to a surface of outer membrane 20. Outer membrane 20 selectively diffuses Mg ions from the test sample so that charged complexes of Mg create potential that can be measured by volt meter 28.

Reagents such as calibration or control reagents may contact outer membrane 20 of Mg sensor 20 through sample path 22. The reagent may include a surfactant. The surfactant may be used to limit surface tension of the calibration or control reagent on outer membrane 20, to enhance membrane wettability on the surface of outer membrane 20, and/or to facilitate bubble dislodging on the outer membrane 20.

The selectivity and sensitivity of iMg sensor 10 to Mg ions may be adversely affected by petroleum-based nonionic surfactants. Petroleum-based nonionic surfactant containing poly(ethylene oxide) subunits complexes magnesium ions when partitioning into membrane 20. Examples of petroleum-based nonionic surfactants are polyoxyethylene lauryl ether (e.g., Brij-35™) and octylphenol ethylene oxide condensate (e.g., Triton X-100®). Alkyl-N-methylglucamide-based non-ionic surfactants, such as N-methyl-noctanoyl-D-glucamine or N-methyl-N-nonanoyl-D-glucamine, can be costly. Accordingly, one or more bio-based surfactants (referred to as "biosurfactants") may be used with example iMg sensor 10. Biosurfactants, such as but not limited to those described herein, do not have an adverse effect, or do not have an appreciable effect, on the selectivity and sensitivity of iMg sensor 10 to Mg ions as do petroleum-based nonionic surfactants. Furthermore, example biosurfactants in this disclosure are typically less costly than alkyl-N-methylglucamide-based non-ionic surfactants.

Biosurfactants are environmentally friendly, biodegradable, and non-toxic and may be classified into high and low molecular weight biosurfactants. Low molecular weight biosurfactant efficiently lower surface and interfacial tension, and high molecular weight biosurfactants are more effective as emulsion-stabilizing agents. Examples of low molecular weight biosurfactants include glycolipids, such as rhamnolipids, sophorolipids, lipopeptidesm, and trehalolipids. These low molecular weight biosurfactants have hydrophilic heads comprised of sugar units linked glycosidically with hydrophobic non-polar parts. Examples of high molecular weight biosurfactants include polysaccharides, lipopolysaccharides, proteins and lipoproteins. Polysaccharide-based biosurfactant can be classified into sorbitan esters, sucrose esters and glucose-based surfactants that include alkyl polyglycosides and fatty acid glucamides.

Examples of other biosurfactants that may be used in the reagent include, but are not limited to, liptopeptides such as surfactin; fatty acids and phospholipids, polymeric matrix biosurfactants; particulate biosurfactants; and bacterial biosurfactants composed of polysaccharides, proteins, lipopolysaccharides, lipoproteins or complex mixtures of these biopolymers.

Commercially available examples of biosurfactants include, but are not limited to, alkyl polyglycoside available under the trademark EcoSense™ 3000 from Dow Chemical®; D-glucopyranose, oligomeric, decyl octyl glycosides available under the trademark Glucopon® 215 from BASF Corporation®; rhamnolipids available under the trademark REWOFERM® SL ONE from Evonik®; D-Glucitol, 1-deoxy-1-(methylamino)-, N-coco acyl derivatives available under the trademark GlucoTain® from Clariant®; rhamnolipids from Jeneil Biotech®, and BioLoop® surfactants from Lankem® Ltd.

The example iMg sensors described herein can be used with any of the biosurfactants listed herein, but are not limited to use only with these biosurfactants. The example iMg sensors described herein may also be used with other biosurfactants, such as alkyl-N-methylglucamide-based non-ionic surfactants.

iMg sensor 10 may be incorporated into a point-of-care (POC) system. POC refers to medical diagnostic testing at or near a point of care—that is, at the time and place of patient care, such as an emergency room or an operating room. An example POC system, such as a clinical (e.g., blood gas) analyzer, may be configured to measure physiologically active form(s) of iMg in biological fluids, such as those described herein using iMg sensor 10.

Figure 2:
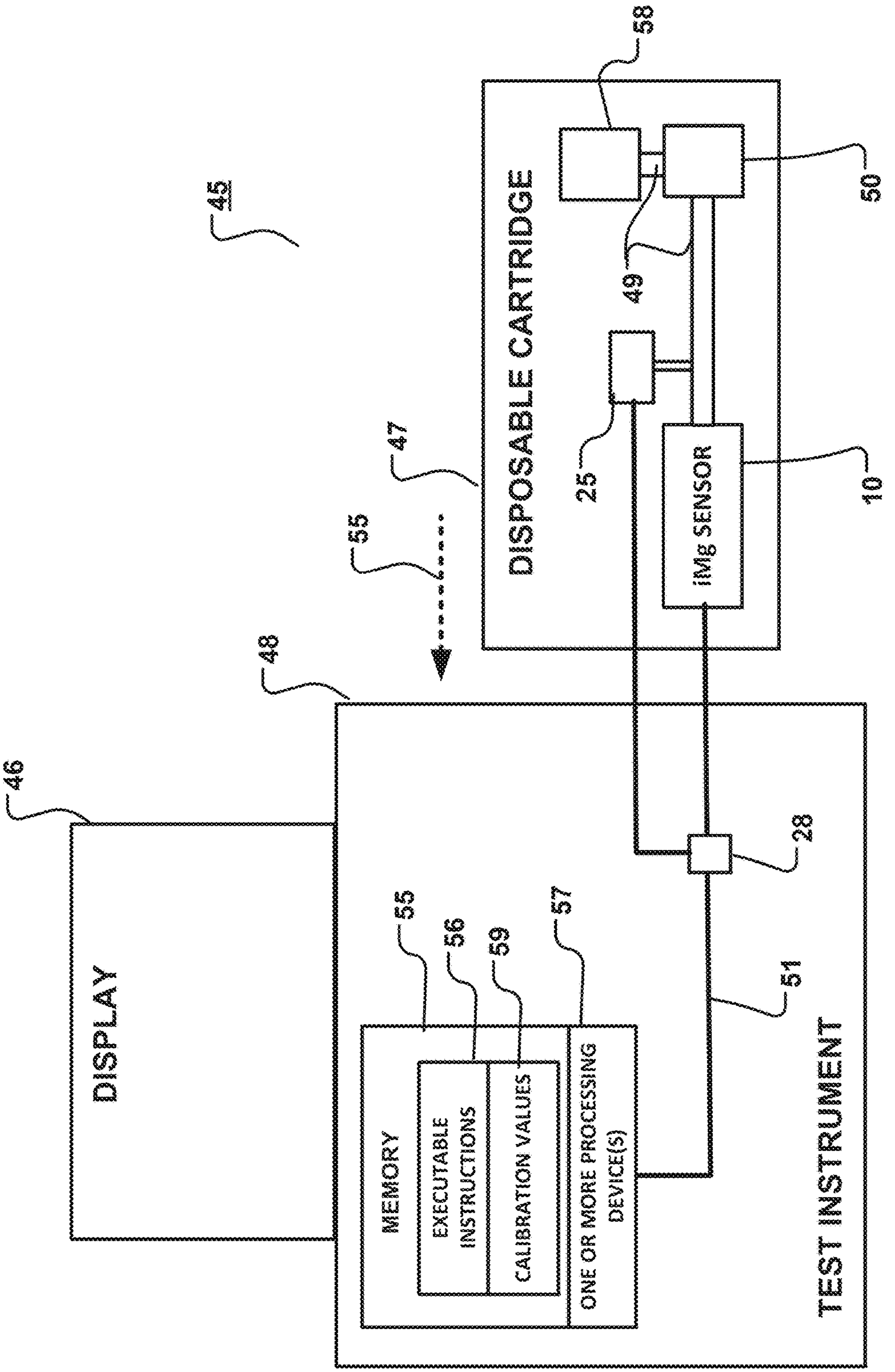
FIG. 2 is a block diagram of an example clinical analyzer system in which the Mg sensor may be incorporated.

FIG. 2 shows a block diagram of an example POC clinical analyzer system ("system") 45 that may contain iMg sensor 10. System 45 may include a test instrument 48 having a display device 46. System 45 also includes a disposable cartridge 47 that slides into test instrument 48 in the direction of dashed arrow 55.

Disposable cartridge 47 may include one or more instances of iMg sensor 10. Disposable cartridge 47 includes a sample receptable 50 for receiving a test sample. Disposable cartridge 47 also contains, in region 58, one or more reagents, such as the calibration and/or control reagents noted above containing one or more biosurfactants such as those described herein. Disposable cartridge 47 includes a fluid path 49, such as one or more ducts or conduits, through which a test sample and/or reagent can be moved via a sample receptable 50 into contact with the sensor card 10 containing iMg sensor 10. Thus, fluid path 49 may run from a location at which a test sample is introduced into the disposable cartridge and/or from a location of one or more reagents and, ultimately to, and may include sample path 22 of iMg sensor 10. Test instrument 48 may contain one or more pumps (not shown) to control flow of fluid through cartridge 47.

Test instrument 48 may include one or more electrically conductive contacts 51 configured to communicate the electrical potential measured by volt meter 28 at structure 24. As described herein, when the test sample contacts outer membrane 20, ionophores in outer membrane form complexes with the Mg ions in the test sample that create an electrical potential that may be measured by volt meter 28.

Test instrument 48 may include memory 55 storing instructions 56 that are executable. Memory 55 may also store calibration values 59 for reagents stored in region 58. Test instrument 48 may include one or more processing devices 57 that execute instructions 56 to determine Mg amounts in a test sample based on electrical potential measurements from iMg sensor 10.

Figure 5:
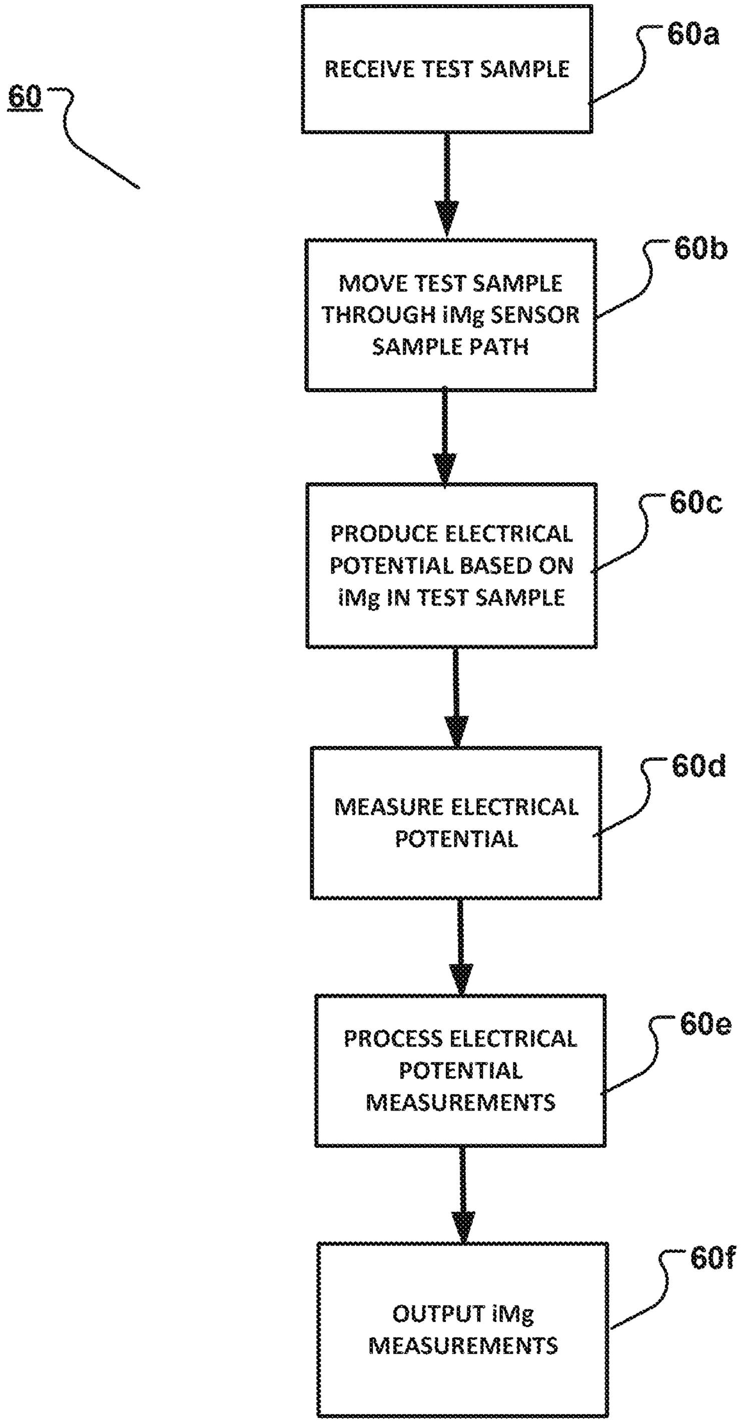
FIG. 5 is a flowchart showing an example process for measuring iMg using the iMg sensor.

FIG. 5 is a flowchart showing an example process 60 for obtaining iMg measurements from a test sample. Test sample is received (60*a*), e.g., in sample receptacle 50. The test sample (with or without reagent) is moved (60*b*), e.g., through pumping, through the fluid path 49 to sample path 22 of iMg sensor 10. At sample path 22, Mg ions in the mixture form complexes with ionophores in outer membrane 22, which charge membrane and create potential (60*c*) that is measured with voltmeter 28 and is proportion to the activity of iMg in the test sample (60*d*). For example, electrical potential at structure 14 is measured relative to a reference electrical potential 29 using volt meter 28.

The measured electrical potential is logarithmically proportional to the level of iMg in the test sample. Electrical potential measurements are processed (60*e*) within instrument 48 to determine the activity or amount of iMg in the test sample. The processing may use the calibration values 59 for the reagents stored in region 58. The iMg measurements, the activity, and/or the amount may be output (60*f*) to display 46 to display graphically on the display 46, or output to a separate computing system (not shown) for processing and/or display.

Figure 3:
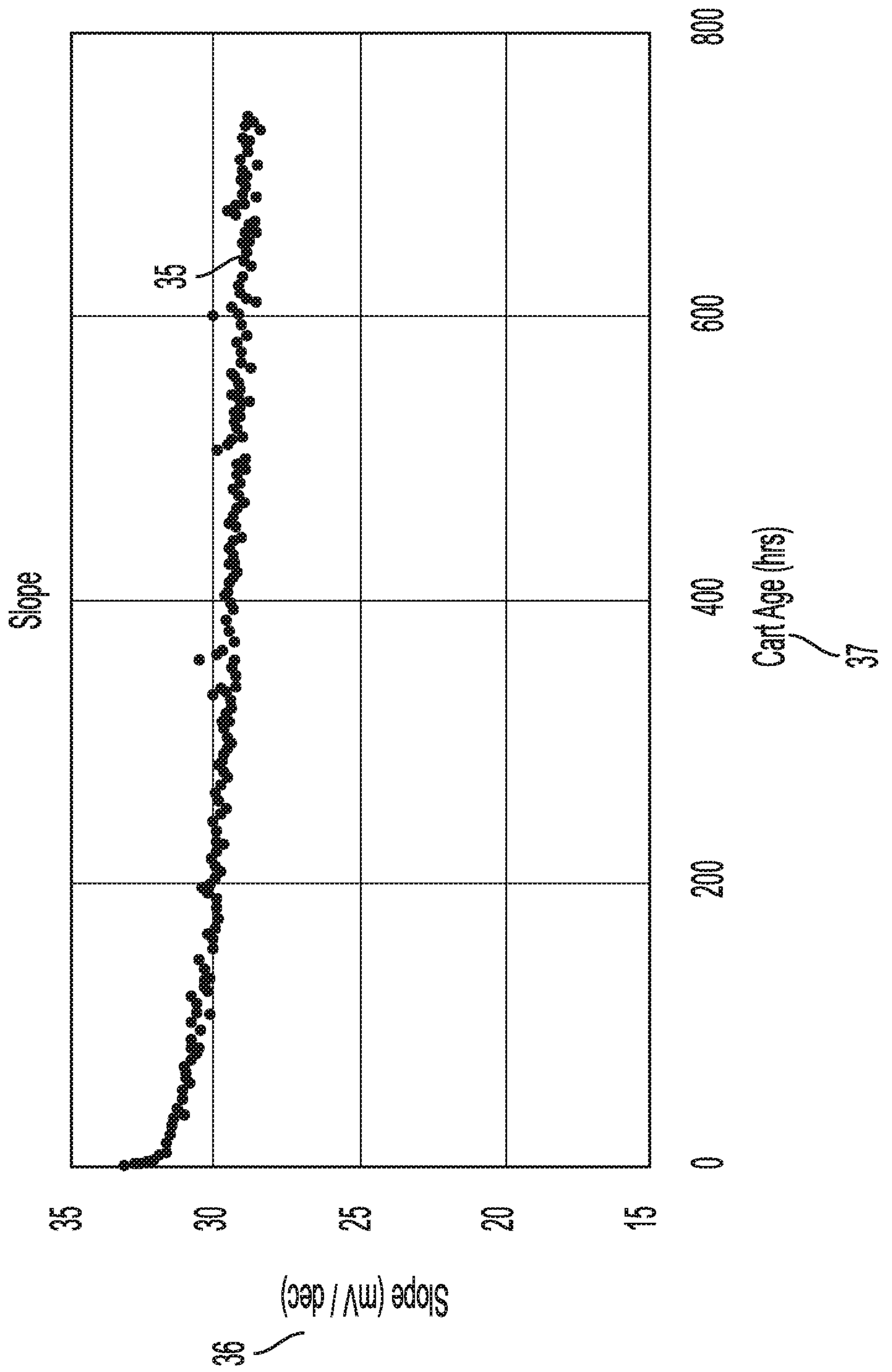
FIG. 3 is a graph showing a Nernstian slope for an example implementation of the Mg sensor.
Figure 4:
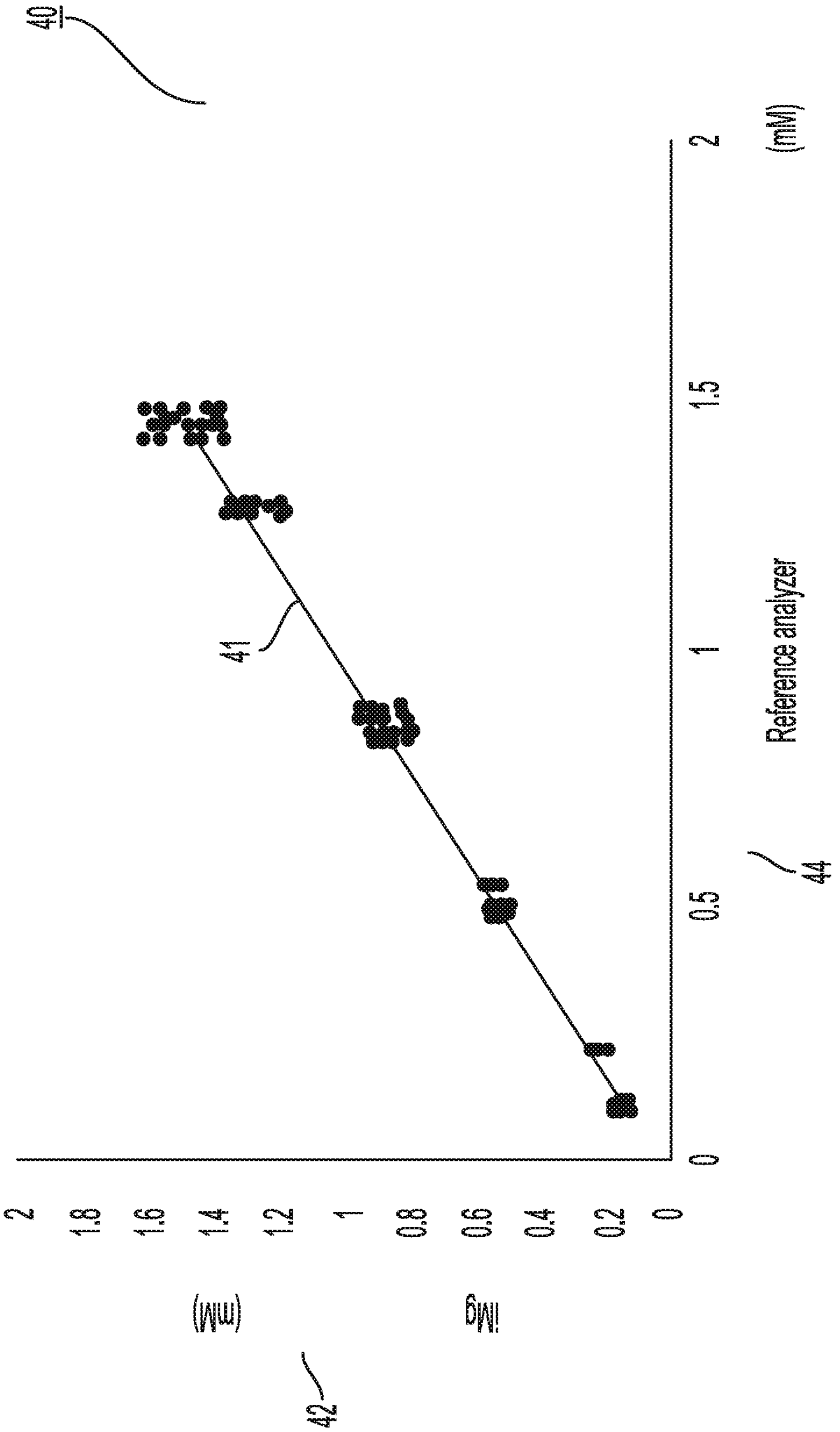
FIG. 4 is a graph showing expected measurements of iMg in a test sample plotted against actual measurements of iMg in the test sample obtained using the iMg sensor.

FIGS. 3 and 4 show plots based on measurements obtained in the foregoing manner from iMg sensor 10 having a membrane with the composition of Table 1.

More specifically, FIG. 3 shows a Nernstian slope 35 over the course of 30 days for iMg sensor 10 having the membrane composition of Table 1. The Nernstian slope measured in millivolts per decade (mV/decade) 36 relative to sensor age ("Cart Age") 37 measured in hours. The Nernstian slope is equal to the change of electrode potential when the concentration iMg in the iMg sensor reaction changes by ten-fold (a decade). The Nernstian slope is an indicator of sensor performance. If the slope changes significantly over time, this may indicate a degradation in sensor performance over that time. As shown, the slope 35 has little change over the period under consideration, which indicates little degradation in sensor performance.

FIG. 4 is a graph 40 showing a plot 41 of expected measurements 42 of iMg in a test sample plotted against actual measurements 44 of iMg in the test sample obtained using iMg sensor 10 having the membrane composition of Table 1 over a range of 0.1 mM to 1.5 mM. The measurements were made using a reference clinical analyzer. The linearity of plot 41 is indicative of the accuracy of iMg sensor 10 over the range, since the measured values at 44 generally match the projected iMg values at 42.

iMg sensor 10 may be incorporated into any clinical analyzer system such as that described in U.S. Pat. No. 6,872,297 (Mansouri), which issued on Mar. 29, 2005, the contents of which are incorporated herein by reference. For example, iMg sensor 10 may be incorporated into the electrode card described in Mansouri.

iMg sensor 10 may be incorporated into any clinical analyzer system, such as the GEM™ 5000 and the GEM Premier ChemSTAT® both by Werfen® S.A.

iMg sensor 10 is provided for illustration sake, and the features described herein are not limited to use with an iMg sensor having the construction of FIG. 1. The iMg sensors described herein are not limited to use in the systems described herein, but rather may be used in any appropriate medical diagnostic system.

The clinical analyzer described herein may be implemented using computing systems or any other appropriate computing device. The clinical analyzer can be implemented, at least in part, using one or more computer program products, e.g., one or more computer program tangibly embodied in one or more information carriers, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the clinical analyzer can be performed by one or more programmable processors executing one or more computer programs to perform the functions described herein. All or part of the control system can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random-access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. A cartridge comprising:

a sensor comprising:

a conductive electrode; and an ion-selective membrane over the conductive electrode, the ion-selective membrane comprising:

an ionophore that is selective for ionized magnesium (iMg); and at least two types of anionic lipophilic salts; and a reagent comprising a biosurfactant.

2. The cartridge of claim 1, wherein the ion-selective membrane comprises 1% to 4% weight-by-weight (w/w) of one or more ionophores.

3. The cartridge of claim 1, wherein the one or more ionophores comprise:

ETH 5506 where ETH 5506 is $C_{63}H_{96}N_6O_6$ (1,3,5-Tris[10-(1-adamantyl)-7,9-dioxo-6,10-diazaundecyl]benzene); or ETH 7025, where ETH 7025 is $C_{49}H_{94}N_6O_6$ (N,N',N"-Tris[3-(heptylmethylamino)-3-oxopropionyl]-8,8'-iminodioctylamine); or K22B5, where K22B5 is $C_{38}H_{60}N_4O_8$ (4,13-[Bis(N-adamantylcarbamoyl)acetyl]-1,7,10,16,tetraoxa-4,13-diazacyclooctadecane).

4. The cartridge of claim 1, wherein the biosurfactant comprises at least one of a high molecular weight biosurfactant or a low molecular weight biosurfactant.

5. The cartridge of claim 4, wherein the low molecular weight biosurfactant comprises at least one of a rhamnolipid, a sophorolipid, or a lipopeptide; and wherein the high molecular weight biosurfactant comprises at least one of a polysaccharide, a lipopolysaccharide, a protein, or a lipoprotein.

6. The cartridge of claim 1, wherein the sensor comprises a sample path adjacent to the ion-selective membrane; and wherein the cartridge comprises a fluid path that runs at least from at least one of a location at which a test sample is introduced into the cartridge or a location of the reagent to the sample path.

7. A system comprising:

a test instrument to receive the cartridge of claim 1;

wherein the sensor comprises a conductive electrode having an electrical potential that is based on an activity of iMg in a test sample;

an electrical contact to measure the electrical potential; and one or more processing devices to determine an amount of iMg in the test sample based on the electrical potential.

8. The system of claim 7, wherein the system comprises a point-of-care clinical analyzer system.

9. The cartridge of claim 1, wherein:

the ion-selective membrane further comprises a plasticizer, and the at least two types of anionic lipophilic salts comprise a mixture of one or more chlorinated borate salts and one or more fluorinated borate salts.

10. The cartridge of claim 9, wherein the at least two types of anionic lipophilic salts are present in the ion-selective membrane at a ratio of 1:1.

11. The cartridge of claim 9, wherein the at least two types of anionic lipophilic salts are present in the ion-selective membrane at a ratio of between 1.5:1 and 2.1:1.

12. The cartridge of claim 9, wherein the ion-selective membrane comprises 1% to 3% weight-by-weight (w/w) of the mixture of one or more chlorinated borate salts and one or more fluorinated borate salts.

13. The cartridge of claim 9, wherein the one or more chlorinated borate salts comprises at least one of: potassium tetrakis(4-chlorophenyl)borate (KTpClPB) or sodium tetrakis(4-chlorophenyl)borate); and wherein the one or more fluorinated borate salts comprises at least one of: tetrakis(4-fluorophenyl)boron sodium (Cesibor), sodium or potassium tetrakis[3,5-bis(trifluoromethyl)phenyl]borate (NaTPB or KTFPB), or sodium or potassium tetrakis[3,5-bis(1,1,1,3,3,3-hexafluoro-2-methoxy-2-propyl)phenyl]borate trihydrate (HFPB).

14. The cartridge of claim 9, wherein the ion selective membrane comprises an outer membrane and a plasticizer comprising a majority of the outer membrane.

15. The cartridge of claim 9, wherein the plasticizer has a log P (partition coefficient) value of between 6.7 and 8.9.

16. The cartridge of claim 9, wherein the ion-selective membrane comprises 60% to 66% weight-by-weight (w/w) of the plasticizer.

17. The cartridge of claim 9, wherein the plasticizer comprises:

ETH 8045 where ETH 8045 is $C_{26}H_{37}NO_3$ ([12-(4-Ethylphenyl)dodecyl]2-nitrophenyl ether); or a mixture comprising ETH 8045 and NPOE, where NPOE is $C_{14}H_{21}NO_3$ (1-(2-Nitrophenoxy)octane); or a mixture comprising ETH 8045 and ETH 217, where ETH 217 is $C_{18}H_{29}NO_3$ (1-Dodecyloxy-2-nitrobenzene, 2-Nitrophenyl dodecyl ether); or a mixture comprising ETH 8045, ETH 217, and NPOE.

18. The cartridge of claim 9, wherein the ion-selective membrane comprises:

an inner membrane comprising a hydrogel; and an outer membrane comprising the ionophore, the at least two types of anionic lipophilic salts, the plasticizer, and a polymeric matrix.

19. The cartridge of claim 9, wherein the sensor has a consistent amount of iMg selectivity and a consistent Nernstian response for at least 30 days.

20. The cartridge of claim 1, wherein the at least two types of anionic lipophilic salts comprise at least one of: potassium tetrakis(4-chlorophenyl)borate (KTpClPB) or sodium tetrakis(4-chlorophenyl)borate); and at least one of: sodium or potassium tetrakis[3,5-bis(trifluoromethyl)phenyl]borate (NaTPB or KTFPB).

* * * * *